United States Patent [19]

Schwartz

[11] 4,278,426
[45] Jul. 14, 1981

[54] RELATOR ASSEMBLY

[76] Inventor: Robert Schwartz, 1271 Westfield Ave., Rahway, N.J. 07065

[21] Appl. No.: 128,046

[22] Filed: Mar. 7, 1980

[51] Int. Cl.³ .............................................. A61C 11/00
[52] U.S. Cl. ...................................................... 433/54
[58] Field of Search .................................... 433/54, 56

[56] References Cited

U.S. PATENT DOCUMENTS

| 2,219,559 | 10/1940 | Lentz | 433/56 |
| 3,423,834 | 1/1969 | Irish | 433/56 |

Primary Examiner—Robert Peshock

[57] ABSTRACT

Duplicatable maxillary denture materials, e.g., partial or complete dentures, wax-ups and bite blocks, are prepared employing the relator assembly and process of the invention. The process involves forming the maxillary denture materials from a rough maxillary cast of the patient's mouth that has a base and an expression of the maxillary alveolar ridge including the anterior palatine papilla and hamular notches. In the process, the cast is suspended over a horizontally extending, flat occlusal base member at a predetermined height corresponding to the proposed incisal length of the denture materials with members of substantially equal height, located on the occlusal table, that contact the cast at the palatine papilla and hamular notches. The base of the suspended rough cast is luted to a maxillary base member that is located over and substantially parallel to the occlusal base member to form a cast whose base is parallel to the hamular-incise plane. Thereafter denture elements, individual artificial teeth or bite-block elements are arranged on the occlusal base member in a predetermined location relative to the cast luted to the maxillary base member and corresponding to the proposed labial drape of the patient. The aforesaid denture elements, individual teeth or bite-block elements are then luted to the alveolar ridge of the cast mounted on the maxillary base member.

4 Claims, 6 Drawing Figures

RELATOR ASSEMBLY

BACKGROUND OF THE INVENTION

1. Field of the Invention

This invention is concerned with a relator assembly and process useful for preparing duplicatable maxillary denture materials, e.g., partial or complete dentures, wax-ups and bite blocks, from a maxillary cast. More particularly, the invention is related to a mechanical assembly and process that can be employed to prepare dentures and the like from prefabricated arch elements or individual teeth in a duplicatable manner.

2. Description of the Prior Art

The relator system and process of the present invention are related to the devices described in U.S. Pat. No. 3,465,443 and U.S. Pat. No. 4,155,163. U.S. Pat. No. 3,465,443 is concerned with a mechanical system for preparing standardized diagnostic dental casts that have a base that is parallel to the hamular-incise plane. U.S. Pat. No. 4,155,163 is directed to a mechanical configuration for the manufacture of dentures or denture elements that are anatomically related to the hamular-incise plane. The device of U.S. Pat. No. 4,155,163 employs the cast material prepared with the techniques of U.S. Pat. No. 3,465,443.

SUMMARY OF THE INVENTION

In accordance with the present invention, duplicatable dentures, wax-ups and bite blocks are prepared from rough maxillary casts. The relator system of the present invention consists of seven cooperating elements, namely (i) a stand member; (ii) a vertically disposed support means (preferably a unitary member) having an upper and lower portion, said upper and lower portions being in a fixed vertical relationship relative to each other, said lower portion being connected to the aforesaid stand member; (iii) an occlusal base member having a horizontally disposed upper surface and adapted to be located above said stand member; (iv) an arch locator, removably positionable on said occlusal base member, adapted to locate artificial teeth, dentures, denture elements or bite block elements in an arch-shaped arrangement on said occlusal base member; (v) adjustment means associated with said occlusal base member adapted to movably locate said arch locator on the upper surface of said occlusal base member; (vi) a maxillary base member, having an upper and lower surface, connected, preferably pivotably connected, to the upper surface of said support means, the lower surface of said maxillary base member adapted to be positioned in a substantial vertical alignment with and preferably in a plane parallel to the upper surface of said occlusal base member; and (vii) cast positioning means located on the lower surface of said maxillary base member.

In the process of the present invention, the aforesaid device is employed to form maxillary denture materials, e.g., partial or complete dentures, wax-ups and bite blocks. In brief, a patient's rough maxillary cast that has a base and an expression of the alveolar ridge including the anterior palatine papilla and hamular notches is mounted over the horizontally extending flat occlusal base member of the relator device, the cast being suspended above the occlusal table at a predetermined height, corresponding to the proposed incisal length of said denture materials in the mouth of the patient, with members of substantially equal height located on said occlusal table that contact the cast at the anterior palatine papilla and hamular notches. The base of the cast so mounted on the occlusal table is then luted to the lower surface of a maxillary base member (including a cast positioning member) which is positioned over and in vertical alignment with the occlusal base member. It is preferred that at least a portion of the surface of the maxillary base member in contact with said luting material lie in a plane parallel to the upper surface of the occlusal base member to form a cast whose base is parallel to the hamular-incise plane. Thereafter denture elements, individual teeth or wax bite-block elements are arranged on the occlusal base member in a predetermined location relative to the anterior palatine papilla of the cast luted to the maxillary base member and corresponding to the proposed labial drape of the denture materials in the mouth of the patient. Finally, the denture elements, individual teeth or wax bite-block elements, as arranged on the occlusal base member, are luted to the alveolar ridge of the cast.

BRIEF DESCRIPTION OF THE DRAWINGS

The invention will be more readily understood by reference to the accompanying drawings in which:

Referring now to the drawings, reference 1 represents the stand member or, alternatively, a mandibular base member having an upper surface 13 and a lower surface. Reference 4 refers to the maxillary base member of the assembly. Maxillary base member 4 has an upper surface and a lower surface 5. To the lower surface 5 of the maxillary base member 4 is connected a cast positioning means comprising a blade member 2 and backing member 3. The cast positioning means may be enclosed within a flask-type structure 11 (see FIG. 3) that can be removed from the maxillary base member 4 and employed during the further manufacture of denture materials. Preferably, the upper surface of the stand member or mandibular base member 1 is also provided with a cast positioning means. As shown in FIG. 1, the blade member 2 extends longitudinally along the lower surface of the maxillary and upper surface of the mandibular base members. In a preferred structure, a hole is bored through the blade member 2 at a location near the longitudinal midpoint of the blade. The hole is adapted to receive a pin member (not shown). The pin is inserted into the hole of the blade member 2 during the operation of luting a rough cast to the maxillary or mandibular base members and affords a means of rigidly positioning the finished cast on the blade structure 2. The pin is removed from the blade hole to remove a cast from the cast positioning means. The cast positioning means depicted in the Figures constitutes but one mode of locating casts, and it is recognized that alternate structures may be used.

Figure 1:
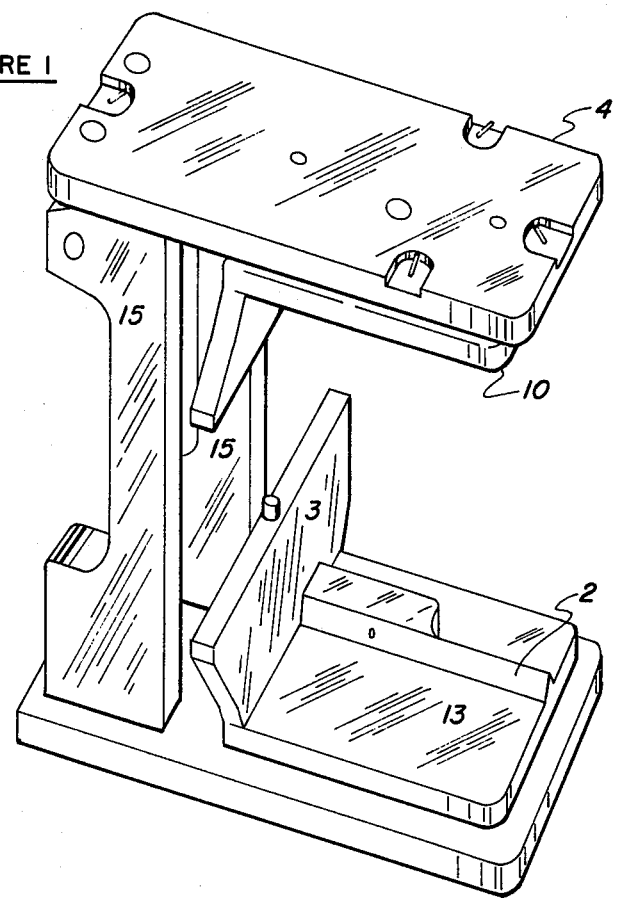
FIG. 1 is a side elevational view of the relator assembly in which the maxillary base member is shown in a closed position.

The maxillary base member 4 is held in position above the upper surface of the stand or mandibular base member 1 by means of a vertically disposed support means 15. The support means 15 has an upper and lower portion which are maintained in a fixed vertical relationship relative to each other, that is, the top and bottom of the support means are not vertically movable in relation to each other. The base of the vertically extending elements of support members 15 are rigidly affixed to the stand member or preferred mandibular base member depicted in the Figures. Preferably the maxillary base member 4 is pivotably mounted on the top portions of support members 15 such that the maxillary base member and cast positioning means can be swung up and away from the stand 1.

Figure 2:
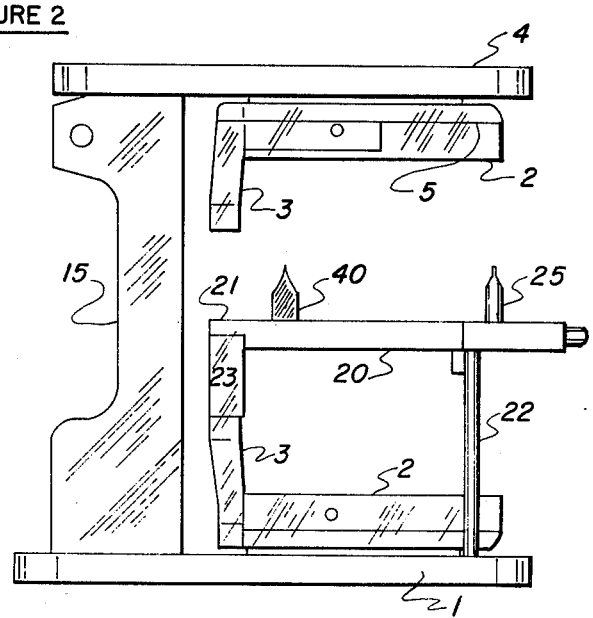
FIG. 2 is a side view of the relator assembly with the occlusal base member and cast supporting or positioning elements in place.

The maxillary base member 4 is arranged on a support structure 15 such that the lower surface 5 of the maxillary base member 4 can be positioned in substantial vertical alignment with and preferably in a plane substantially parallel to the upper surface 21 of occlusal base member 20 and upper surface 13 of mandibular base member 1 when said occlusal base member is positioned above the stand or mandibular base member 1. When the maxillary base member 4 is in the closed position (see FIG. 2), the distance between lower surface 5 and the upper surface 21 of the occlusal base member is fixed and may vary from about 45 to 60, preferably 50 to 55 millimeters.

The occlusal base member 20 is adapted to be located above the stand member or mandibular base member 1. As noted above, the upper surface 21 of the occlusal base 20 is maintained preferably in a plane parallel to lower surface 5 of maxillary base member 4 when the maxillary base member is in the closed position (see FIGS. 1 and 2). In addition, the upper surface 21 is also preferably maintained in a plane parallel to upper surface 13 of the mandibular base member 1. In one arrangement, the occlusal base 20 is located in position by means of forward legs 22 and support member 23 which rests upon backing member 3 of the cast positioning means located on mandibular base member 1.

Figure 4:
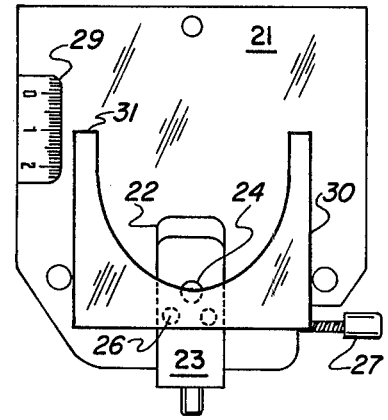
FIG. 4 is a top view of the occlusal base member showing the arch locator member in place on the upper surface of the occlusal base.

A notch or opening 22 of predetermined length and width is machined into the forward portion of the upper surface 21 of occlusal base member 20. Opening 22 is adapted to receive element 23 which slides within opening 22. The upper surface of element 23 is preferably flush with or lies below the upper surface 21 of occlusal base member 20. Element 23 is adapted to receive and retain within hole 24 pin holder elements 25 (when arch locator element 30 is not in place on the upper surface of the occlusal base member.) Similarly, as shown in FIG. 4, element 23 is adapted to movably locate arch locator 30 on the upper surface 21 of the occlusal base member. Preferably, arch locator 30 has two studs located on the under surface thereof which are positioned within holes 26 of element 23 when the same is located on the upper surface of the occlusal base member. Element 23 may be retained in position at any particular spot within opening 22 by means of set screw 27.

Arch locator 30 may be a single component as is shown in FIG. 4 or may be made up of a plurality of components. The function of arch locator 30 is to permit the facile arrangement of full or partial maxillary denture elements, individual teeth, or wax bite-block components on the upper surface of the occlusal base member in a predetermined arch-shaped structure. The maxillary arch defined by the inner periphery of the arch locator 30 preferably corresponds to a standard dental arch form (Hawley arch form) and may, accordingly, be of varying dimensions. Preferably a scale 29 is also superimposed upon the upper surface of the occlusal base member. The scale is used to determine the extent to which element 23 is withdrawn from opening 22. This is accomplished by noting the point where an imaginary line passing across the innermost portion 31 of arch locator 30 intersects scale 29. In the most preferred embodiment, arch locator 30 is sized such that the innermost portion thereof 31 is at the "zero" point on the scale when the element 23 is fully engaged within opening 22.

Figure 5:
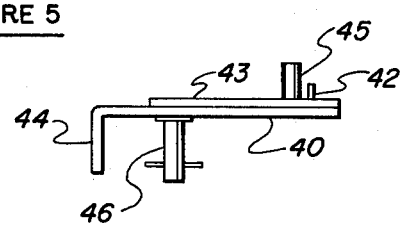
FIG. 5 is a side view of the labial drape locator.
Figure 6:
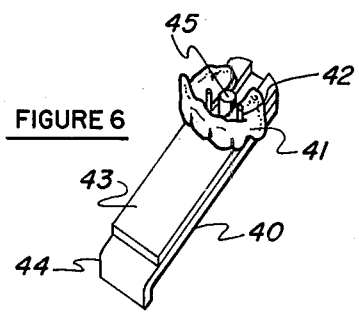
FIG. 6 is a top view of the labial drape locator.

The process and apparatus of the present invention are principally concerned with the manufacture of duplicatable upper dentures, etc., using rough maxillary casts and measurements of the patient's desired incisal length and labial drape. Incisal length and labial drape measurements are secured using the labial drape locator 40 that is depicted in FIGS. 5 and 6. The measurements are secured by mounting a model 41 of six anterior maxillary teeth of a preselected arch size on studs 42 that are located on the upper segment 43 of the labial drape locator 40. Upper segment 43 is adapted to slide across the upper surface of lower segment 44 of the labial drape locator such that model may be moved to and away from pin 45 which is positioned upon lower segment 44.

Labial drape and incisal length measurements are secured by placing a pin 45 of pre-selected height, usually within the range of 4 to 20 millimeters in height, within an opening (not shown) in lower segment 44 that is adapted to receive pin 45. Further, a model 41 of predetermined arch width that is approximately suitable for the patient is mounted on studs 42. The labial drape locator is then placed within the patient's mouth with the top of pin member 45 resting against the anterior palatine papilla of the patient. Pins of varying heights may replace the original pin 45 until the proposed incisal length of the model (which correspond to the denture materials to be produced) in the patient's mouth is secured. Labial drape measurements are obtained by increasing or decreasing the horizontal distance between pin member 45, which is positioned on the patient's anterior palatine papilla, relative to the front portion of model 41 by making appropriate adjustments of the upper segment 43 and lower segment 44 of the labial drape locator 40. After an appropriate labial drape (upper lip placement relative to the outer surface of model 45) is secured, the upper and lower segments of the device are locked into position relative to each other using a screw member 46. The labial drape decided upon using the labial drape relator 40 corresponds to the proposed labial drape of the denture materials to be produced using the process and apparatus of the invention. The incisal length measurements (height of pin 45 above the upper surface 43 of the labial drape locator 40) and labial drape measurement (horizontal distance between the anterior most portion of model 41 and the anterior most portion of pin 45) are subsequently recorded and used thereafter in the process of this invention.

As noted previously, the present invention is concerned with an apparatus and process for making duplicatable maxillary denture materials from a rough maxially cast that has a base and an expression of the alveolar ridge including the anterior palatine papilla and hamular notches. Such a cast is secured by first obtaining a maxilla impression that includes a good outline of the hamular notches and the anterior palatine papilla. The rough cast is prepared by pouring plaster or other suitable casting media into the initial impression. With the process of the present invention, the rough cast 50 (FIG. 3) is mounted over the upper surface 21 of the horizontally extending, flat occlusal base member 20. The cast is suspended above the occlusal table at a predetermined height corresponding to the previously measured incisal length of the patient. Preferably the rough cast is suspended above the occlusal base member 20 with members of substantially equal height located on the occlusal base member that contact the cast at the anterior palatine papilla and hamular notches. In a most preferred structure, depicted in FIGS. 2 and 3, the rough cast is suspended above the occlusal table using pin holder 25 and knife edge 40. Preferably the hamular notches of the cast rest on knife edge 40 and the midpoint of the anterior palatine papilla rests upon pin holder 25. In the most preferred operation, a thin pin is placed into the midpoint of the anterior palatine papilla of the cast 50 which in turn is placed within an internal axial bore (not shown) of pin holder 25, thereby fixing the position of the rough cast on pin holder 25. Knife edge 40 is preferably not physically attached to the occlusal base member.

In mounting the cast 50, element 23, which supports pin holder 25, is extended completely into opening 22 of the occlusal base member 20. In that position, the pin holder preferably lies immediately below the blade member 2 of the cast positioning means located on the lower surface of the maxillary base member 4. Since the pin holder 25 and knife edge 40 are of the same height, a height corresponding to the proposed incisal length of the denture materials in the mouth of the patient, the anterior palatine papilla and the hamular notches (which define the hamular-incise plane) therefore lie in a plane parallel to the upper surface of the occlusal base member 20. As so suspended, the cast is positioned at a height such that the location of the rough cast above the occlusal table is the same height as the patient's alveolar ridge is above the proposed occlusal surface of the patient's proposed maxillary denture materials.

Figure 3:
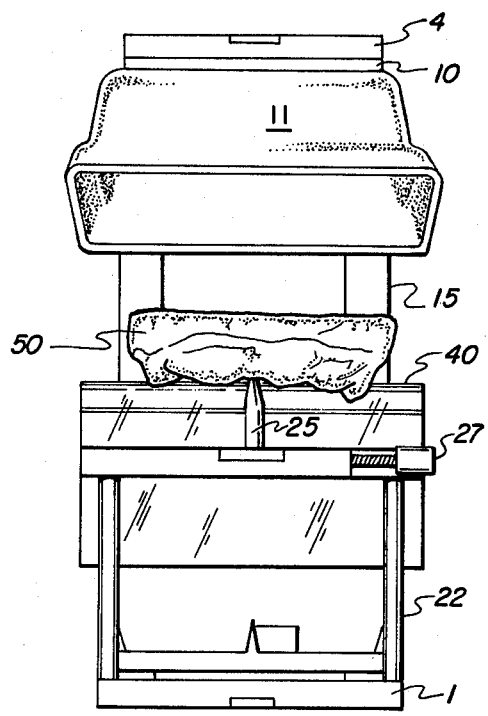
FIG. 3 is a front view of the relator assembly in which the maxillary base member is shown in a raised position and a flask element is in place on the maxillary base member.

Thereafter the base of the rough cast, mounted as indicated above on the knife edge and pin holder, is luted to the cast positioning means of the maxillary base member that is positioned over and in vertical alignment with the occlusal base member. It is preferred that the planar surface 5 of the maxillary base member 4 be maintained parallel to the upper surface 21 of the occlusal base member 20. When such a configuration is employed, the resulting cast or structure formed by luting the base of the rough cast to the maxillary base member results in the formation of a structure or cast whose base is parallel to the hamular-incise plane. It should be noted that the cast positioning means may be partially enclosed within flask 11 as is shown in FIG. 3.

After completion of the attachment of the rough cast to the cast positioning means located on the maxillary base member, the knife edge 40 and pin holder 25 are removed from the upper surface of the occlusal base member and an appropriately sized arch locator 30 is located upon element 23. Thereafter element 23 is withdrawn from opening 22 by a distance corresponding to the labial drape distance measured previously using the labial drape locator 40. In a preferred embodiment, this distance is determined by referencing the location of the terminal portion 31 of arch locator 30 to scale 29. After the element 23 has been withdrawn from opening 22 the proper distance, this position is fixed using set screw 27 which bears against element 23. Thereafter individual teeth or complete or partial prefabricated dentures or wax bite-block elements are located within the inner periphery of the arch locator 30 with the occlusal surface of the individual teeth, etc., being set in place on the upper surface 21 of the occlusal base member 20. The arch locator 30 functions to position the individual teeth, etc., on the occlusal base member 20 in a fixed position relative to the location of the anterior palatine papilla of the maxillary cast that is luted to the cast positioning means on the maxillary base member.

The final step in the process consists of luting the denture elements or individual teeth as arranged on the upper surface of the occlusal base member to the alveolar ridge of the cast that is connected to the maxillary base member. This latter step may be conducted by placing a sufficient quantity of wax on top of the artificial teeth or denture elements positioned by the arch locator 30 and then pivoting the maxillary cast onto the wax. It is preferred that plaster be used in luting the rough cast to the cast positioning means and that wax be employed to lute or connect the denture elements or individual teeth to the alveolar ridge of the cast. When making duplicatable bite blocks, wax or wax-like material is located within the arch locator 30 rather than artificial teeth or full or partial artificial dentures. The luting or connection of wax bite-block elements to the alveolar ridge of the maxillary cast is accomplished by simply pivoting the cast onto the wax located within the arch locator 30.

The cast/artificial teeth or denture composites formed by the process and device of the present invention can be processed using techniques well known to those skilled in the art to form maxillary dentures. One such method is disclosed in U.S. Pat. No. 4,155,163. After the maxillary denture is formed, the mandibular denture can be formed using any of the usual mechanisms that serve to establish the relationship of the lower jaw to the upper denture or bite block manufactured in accordance with the process of the present invention.

What is claimed is:
1. A relator assembly useful for making maxillary denture materials comprising:
(a) a stand member;
(b) a vertically disposed support means having an upper and lower portion, said upper and lower portions being in a fixed vertical relationship relative to each other, said lower portion connected to said stand member;
(c) an occlusal base member having a horizontally disposed upper surface and adapted to be located above said stand member;
(d) an arch locator, removably positionable on said upper surface of the occlusal base member, adapted to locate artificial teeth, denture elements or bite block elements in a fixed position and in an arch-shaped arrangement on said occlusal base member;
(e) adjustment means associated with said occlusal base member adapted to movably locate said arch locator on the upper surface of said occlusal base member;
(f) a maxillary base member having an upper and lower surface, connected to the upper portion of said support means, the lower surface of said maxil- lary base member adapted to be positioned in substantial vertical alignment with said occlusal base member; and (g) cast positioning means located on the lower surface of said maxillary base member.

2. The relator assembly of claim 1 wherein at least a portion of the lower surface of the maxillary base member lies in a plane parallel to the upper surface of said occlusal base member.

3. A process for making maxillary denture materials from a rough maxillary cast of the patient's mouth, said cast having a base and an expression of the alveolar ridge including the anterior palatine papilla and hamular notches, which comprises:

(a) suspending said rough cast over a horizontally extending, flat occlusal base member, said cast suspended above said occlusal base member at a predetermined height corresponding to the proposed incisal length of said denture materials in the mouth of the patient, with members of substantially equal height, located on said occlusal base member, that contact the cast at the anterior palatine papilla and hamular notches;

(b) luting the base of said rough cast to a maxillary base member positioned over and in vertical alignment with the occlusal base member;

(c) arranging denture elements or individual teeth or bite-block elements on the occlusal base member in a predetermined location relative to the anterior palatine papilla of said cast luted to said maxillary base member and corresponding to the proposed labial drape of said denture materials in the mouth of the patient; and (d) luting the denture elements, individual teeth or bite-block elements as arranged on the occlusal base member to the alveolar ridge of said cast.

4. The process of claim 3 wherein at least a portion of the surface of the maxillary base member in contact with said luting material is located in a plane parallel to the occlusal base member to form a cast whose base is parallel to the hamular-incise plane.

* * * * *